United States Patent [19]

Iwahashi

[11] Patent Number: 5,009,887

[45] Date of Patent: Apr. 23, 1991

[54] DEODORANT COMPOSITION IN THE FORM OF A GEL

[75] Inventor: Takashi Iwahashi, Sagamihara, Japan

[73] Assignee: Aikoh Co., Ltd., Tokyo, Japan

[21] Appl. No.: 388,023

[22] Filed: Jul. 31, 1989

Related U.S. Application Data

[63] Continuation-in-part of Ser. No. 256,561, Oct. 12, 1988, abandoned.

[51] Int. Cl.$^5$ .............................................. A61K 31/78
[52] U.S. Cl. ............................ 424/76.1; 252/357; 422/5; 424/76.21; 424/76.3; 424/76.5; 424/76.6; 424/76.7; 424/81; 424/486
[58] Field of Search .......................... 422/5; 252/357; 424/76.1, 76.2, 76.3, 76.5, 76.6, 76.7, 81, 486

[56] References Cited

U.S. PATENT DOCUMENTS

| | | | |
|---|---|---|---|
| 3,769,398 | 10/1973 | Hewitt | 424/70 |
| 4,058,597 | 11/1977 | Passedouet et al. | 424/47 |
| 4,075,350 | 2/1978 | Michaels | 252/106 |
| 4,145,436 | 3/1979 | Michaels | 252/106 |
| 4,154,818 | 5/1979 | Kanada et al. | 424/81 |
| 4,183,952 | 1/1980 | Michaels | 424/65 |
| 4,229,410 | 10/1980 | Kosti | 424/76.7 |
| 4,590,249 | 5/1986 | Cabestany et al. | 424/70 |
| 4,666,671 | 5/1987 | Purzycki et al. | 424/76.7 |

FOREIGN PATENT DOCUMENTS

| | | | |
|---|---|---|---|
| 0160738 | 12/1979 | Japan | 424/76.7 |
| 0036057 | 2/1985 | Japan | 424/76.6 |
| 0119950 | 6/1985 | Japan | 424/76.7 |
| 1172561 | 8/1986 | Japan | 424/76.8 |

*Primary Examiner*—Ellis P. Robinson
*Assistant Examiner*—Archene A. Turner
*Attorney, Agent, or Firm*—Larson & Taylor

[57] ABSTRACT

A new deodorant composition in the form of gel is now provided, which comprises 2% to 30% by weight of sodium polyacrylate or ammonium polyacrylate having a molecular weight of form 40,000 to 300,000, 1% to 10% by weight of diglycidyl ether or polyglycidyl ether, 5% to 40% by weight of deodorizer containing as active ingredients ethanaminium N-(carboxymethyl)-2-hydroxy-N, N-bis(2-hydroxyethyl)choride, diethanolamine, triethanolamine and glyoxal, and the remainder of water.

The gel typed deodorant composition according to this invention may effectively be used to deodorize acidic and alkaline bad odors in the enclosed areas.

3 Claims, No Drawings

1

DEODORANT COMPOSITION IN THE FORM OF A GEL

SUMMARY OF THE INVENTION

This application is a continuation in part of application Ser. No. 256,561 filed on Oct. 12, 1988, now abandoned.

This invention relates to a new deodorant composition in the form of gel in which a deodorizer is gelled by using a gelling agent and which may merely be placed at the sources of generating malodors such as refrigerator, toilet area, rooms in houses and vehicles to deodorize malodors. The gel typed deodorant composition according to this invention is very effective for deodorizing acidic odor-generating substances such as hydrogen sulfide and methylmercaptan as well as alkaline odor-generating substances such as ammonia and trimethylamine because the gel contains a deodorizer which acts on malodors through chemical reactions.

BACKGROUND OF THE INVENTION

There are already known a lot of patent literatures relating to deodorant compositions which may mainly be classified into the four species mentioned below.

(i) Deodorizer which appeals to human's sense, i.e. odor feeling.
(ii) deodorizer which exhibits deodorization activity due to physical adsorption action.
(iii) deodorizer which exerts deodorization activity by the use of microorganism.
(iv) deodorizer which shows deodorization activity due to the mechanism of chemical reaction.

More specifically, the deodorizer of the first type is the one which utilizes a masking method by fragrant materials. According to the nature of bad odors, however, this method has a drawback that unpleasant bad odors may sometimes be promoted by the fragrant materials employed. Moreover, the deodorizer of the second type contains an active carbon as main ingredient and so has disadvantages that it is poor to moisture content and that it may also adsorb pleasant smells to human beings. Furthermore, the deodorizer of the third type suffers from drawbacks that it has a weak activity on immediate deodorization effect and is often difficult to control under appropriate conditions. Whereas, the deodorizer of the fourth type has remarkable advantages that is takes fast-acting deodorization effect, is very easy to handle and safe by the appropriate choice of active reagent to be used and may cause the desired deodorization efficiency to be ensured.

This invention provides a deodorant composition in the form of gel into which a deodorizer acting on malodors through chemical reactions is incorporated. The sources generating foul-smelling gases are in refrigerators, toilet area such as that in households, motor vehicles, buses or aircrafts and in automobiles, which may in each case form enclosed areas very poor in diffusion efficiency of foul-smelling gases. It is desirable to spray as avoidably as possible the enclosed area with a deodorizing reagent. As an alternative to spraying the deodorizing reagent, the use of either active carbon of fragrant materials is most commonly conducted. The active carbon, while of course having a deodorization capacity, suffers from disadvantages. In addition to its degradation due to moisture content, it often shows a reduced deodorization activity when foul-smelling gases are actually generated in the enclosed area, because it may randomly adsorb not only malodors but also sweet smells exerted from fragrant reagents and bad-odorless smell. Whereas, a deodorant composition in the form of gel and containing therein a deodorizer acting on malodors through chemical reactions has advantages that it reacts selectively with only bad odors dependent upon the nature of deodorizing reagents contained therein and that the time of exchanging the deodorant composition can be determined when examined visually, because the water content contained in the gel evaporates with the lapse of time and the gel is thereby reduced in size. Moreover, it is also possible to use a deodorization method wherein a liquid deodorizer held in a container is positioned at the sources generating foul-smelling gases to deodorize said smells, but this method suffers from a drawback that the liquid deodorizer readily flows out of the container and with which peripheral circumstances are contaminated when the container is subjected to vibration or falling down thereof. When the liquid deodorizer is gelled to make a gel, such problems as mentioned above can be totally eliminated. Furthermore, there are some commercially available gel-typed deodorant compositions at the present time, but these commercial products are poor in deodorization activity (please refer to Example 3 below).

We, the present inventors, have made extensive researches in an attempt to seek for such deodorant composition as dissolving above problems, and we have now found that there may be obtained a novel, chemically reacting deodorant composition in the form of gel which comprises a gel forming material, a gelling agent, a chemically reacting deodorizer containing as active ingredients a betaine compound an alcoholic amine compound and an aldehyde compound, and water in specific proportions.

DETAILED DESCRIPTION OF THE INVENTION

According to an aspect of this invention, therefore, there is provided a deodorant composition in the form of gel, which comprises 2% to 30% by weight of sodium polyacrylate or ammonium polyacrylate having a molecular weight of from 40,000 to 300,000, 1% to 10% by weight of diglycidyl ether or polyglycidyl ether, 5% to 40% by weight of deodorizer containing as active ingredients ethanaminium N-(carboxymethyl)-2-hydroxy-N,N-bis(2-hydroxyethyl) chloride, diethanolamine, triethanolamine and glyoxal, and the remainder of water.

The term "gel" herein is meant "a setup state of colloidal particles or high molecular solute wherein these particles or solute becomes an agglomerated structure with the result of losing independent motility because of its interaction" as described in the literature "Encyclopaedia Chimica" published by Kyoritsu Shuppan Co. (1981). We can find in daily life many gel products such as food products e.g. bean curd, devil's tongue jelly, boiled fish paste, pudding, jelly and boiled egg, as well as household articles e.g. paper diapers, menstruation articles and fragrant compositions. The gel forming substances may primarily be classified into natural ones and synthetic ones and typical examples of these substances include the following:

(i) Natural gel forming substances: agar-agar, gelatin, egg white, starch, caragenane, sodium alginate and the like.

(ii) Synthetic gel forming substances: polyvinyl alcohol, carboxymethylcellulose, sodium polyacrylate, polyacrylamide and the like.

The mechanism of gelation wherein a gel forming substance is converted into a gel product is understood to occur in the following manner. Gelation of natural gel forming substance generally takes place dependent upon the intermolecular force of its high molecule and shows a reversible behavior between gel and sol upon heating and cooling. Whereas, gelation of synthetic gel forming substance results in three-dimentional network or reticulation either by crosslinking reaction caused by light or radiation or by the use of crosslinking agent. The geletion of synthetic gel forming substance is very poor in reversibility between gel and sol due to variation in temperature as occurring in the natural substance and rather called as irreversible, because the bond of crosslinked point in the gelled product made of the synthetic gel forming substance is formed by covalent bond. We have found widespread applications in refrigerator, toilet area, automobile chamber and the like, to which the gel-formed deodorant composition according to this invention is intended to be used. In such uses, the temperature at which the deodorant composition of this invention is envisaged to encounter varies over a fairly wider, severe range of from 0° to 70° C. For example, a higher temperature of 50° to 70° C. is encountered in an automobile chamber under parking in the summer seasons and a lower temperature of 0° to 4° C. encountered in refrigerators. Therefore, it is not preferred that the gelled product should possess a reversibility between gel and sol upon heating and cooling, as appearing in natural gel forming substances. By virtue of these reasons, we have selected a natural gel forming substance which reveals no reversibility between gel and sol in temperature variation and a crosslinking agent, and tried to incorporate a specific deodorizer into the resulting gel. Commercially available sodium polyacrylate or ammonium polyacrylate is to be used as the gel forming substance, and the molecular weight thereof is 10,000, 40,000, 140,000 and 280,000. As illustrated in Example 1 below, however, it has proved that the sodium polyacrylate or ammonium polyacrylate having a molecular weight of 10,000 is unfit for actual use and we have excluded this polyacrylate from the deodorant composition according to this invention. In the deodorant composition of this invention, the proportion of the gel forming substance is limited to a specific range of from 2% to 30% by weight based on the total composition, since it is the preferred range to obtain a desirable gel.

An aldehyde compound, amine compound, oxirane compound and the like are commonly used as crosslinking agents, but we have selected an oxirane compound in the deodorant composition of this invention, since other aldehyde compounds and amine compounds are unsuitable to use because of their severe foul odors. Further, we have particularly selected a commercially available product, diglycidyl ether or polyglycidyl ether as the oxirane compound. Typical examples of diglycidyl ether include ethylene glycol diglycidyl ether, polyethylene glycol diglycidyl ether, propylene glycol diglycidyl ether, polypropylene glycol diglycidyl ether and neopentyl diglycidyl ether, and typical examples of polyglycidyl ether include trimethylolpropane polyglycidyl ether, polyglycerol polyglycidyl ether, glycerol polyglycidyl ether and diglycerol polyglycidyl ether. In the deodorant composition according to this invention, the proportion of the crosslinking agent is restricted to a specific range of from 1% to 10% by weight based on the total composition, since it is the preferred range to obtain an appropriate gel.

In preparing the gel-like deodorant composition of this invention, we have used a commercially available preparation "Epoleon (registered trade mark)N-100 Type, trade name of the applicant's product" as the chemically reacting deodorizer containing as active ingredient a betaine compound. The proportion of the chemically reacting deodorizer employed is limited to a specific range of from 5% to 40% by weight based on the total composition, and any proportion of the deodorizer falling within this range may optionally be selected in relationship with the strength of gel (as to whether or not the gel is constantly maintained in its form). The reason why we have selected this deodorizer resides in that amongst the chemically reacting deodorizers, Epoleon N-100 is particularly effective for deodorization of alkaline odor gases such as ammonia or trimethylamine (TMA) as well as acidic odor gases such as hydrogen sulfide or methylmercaptan (MeSH), and that it is a colorless, clear, odorless liquid and it does not tint the resulting gel when incorporated therein. Whereas, the commercially available deodorizers called as natural extracts often exert a characteristic malodor.

The applicant's three commercial products "Epoleon ER-10 type", "Epoleon N-100 type" and "Epoleon S type" deodorizers as given in Table 1 below are tested on their deodorization activities. Comparison to the four, commercially available, solution typed deodorizers ex A to D companies. The comparative test results (concentrations of remaining odor gas in ppm) concerning deodorization capacities of these deodorizers are summarized in Table 1 below.

TABLE 1

| Deodorizer | Content of active ingredient | Appearance | Odor | pH | $NH_3$ (ppm) | TMA (ppm) | $H_2S$ (ppm) | MeSH (ppm) |
|---|---|---|---|---|---|---|---|---|
| ER-10 type | 35% by weight | Colorless, Clear | No | 4.0 | 0 | 0 | 35 | 20 |
| N-100 type | 27% by weight | Colorless, Clear | No | 6.2 | 5 | 0 | 10 | 1 |
| S type | 17% by weight | Colorless, Clear | No | 10.0 | 950 | 90 | 0 | 20 |
| Product ex A company | 20% by weight | Greenish brown | No | 1.1 | 90 | 0 | 1000 | 60 |
| Product ex B company | 32% by weight | Dark yellow | Yes | 5.0 | 150 | 10 | 40 | 25 |
| Product ex C company | 17% by weight | Dark yellow | Yes | 10.5 | 950 | 90 | 20 | 50 |
| Product ex D company | 5% by weight | Blue | Yes | 4.0 | 850 | 20 | 100 | 60 |

TABLE 1-continued

| Deodorizer | Content of active ingredient | Appearance | Odor | pH | $NH_3$ (ppm) | TMA (ppm) | $H_2S$ (ppm) | MeSH (ppm) |
|---|---|---|---|---|---|---|---|---|
| Blank | — | — | — | — | 950 | 90 | 1000 | 60 |

The test procedure employed is as follows: The deodorization test is carried out by the head space method with the use of a 500 ml conical flask.

(1) The amount of deodorizer employed = 1.0 ml
(2) The amount of water = 10.0 ml (This water is used so as to intermix the deodorizer evenly in the flask under shaking.)
(3) Temperature used = ambient temperature (25° C.)
(4) Shaking period = 5 minutes
(5) The concentration of the malodor gas = as enumerated in Table 1 above in the form of blank values. (1.0 ml of each malodor gas solution previously prepared is weighed into the flask.)
(6) The method of concentration determination = use of Kitagawa typed gas detecting tube.

For the determination of respective liquid proportions, a transfer pippet is used to this end. As obvious from Table 1 above, it is concluded that "Epoleon N-100 type deodorizer" is suitable as active deodorization ingredient for incorporation into the gel, when viewed collectively from the appearance, odor, pH and deodorization capacities of the deodorizers used.

In preparing the gel-like deodorant composition of this invention, therefore, we have selected a commercially available "Epoleon N-100 type deodorizer" which comprises as active deodorization ingredients ethanaminium N-(carboxymethyl)-2-hydroxy-N,N-bis(2-hydroxyethyl)chloride, a mixture of diethanol amine with triethanolamine, and glyoxal. Namely, this Epoleon N-100 type deodorizer contains therein ethanaminium N-(carboxymethyl)-2-hydroxy-N,N-bis(2-hydroxyethyl)chloride as a betaine compound, a mixture of diethanolamine with triethanolamine as an alcoholic amine compound, glyoxal as an aldehyde compound, sodium citrate and sodium dihydrogen phosphate as buffering agent and pH controlling agent, respectively, and water.

The relative proportion of each component in Epoleon N-100 type deodorizer may be as follows:

| | |
|---|---|
| (a) ethanaminium N-(carboxymethyl)-2-hydroxy-N,N-bis(2-hydroxyethyl) chloride | 5 to 20% by weight |
| (b) diethanolamine | 1 to 10% by weight |
| (c) triethanolamine | 0.5 to 5% by weight |
| (d) glyoxal | 0.5 to 5% by weight |
| (e) sodium citrate | 0.5 to 5% by weight |
| (f) sodium dihydrogen phosphate | 1 to 10% by weight |
| (g) water | balance |

Ethanaminium N-(carboxymethyl)-2-hydroxy-N,N-bis(2-hydroxy-N,N-bis(2-hydroxyethyl)chloride used as one of active deodorization ingredients can be prepared by the addition reaction of ethylene oxide (2 mol), ethylene imine (1 mol), water (1 mol) and monochloroacetic acid (1 mol) in an aqueous phase, and has such a betaine structure as shown in the formula:

$$\begin{array}{c} HOCH_2CH_2 \\ HOCH_2CH_2-N^{\oplus}\phantom{xx}-CH_2COO^-H^+ \\ HOCH_2CH_2\phantom{xxxxx}Cl^{\ominus} \end{array}$$

Further, the mechanism of deodorization reaction wherein "Epoleon N-100 type deodorizer" exerts the desired effect on different foul-smelling substances is understood to proceed as follows:

$$-COOH + NH_3 \longrightarrow -COONH_4 \quad \text{(i)}$$

$$-COOH + N(CH_3)_3 \longrightarrow -COONH(CH_3)_3 \quad \text{(ii)}$$

$$NH + H_2S \longrightarrow >\overset{\oplus}{N}H_2 \quad \text{(iii)}$$
$$\phantom{xxxxxxxxxxxxxxx} SH^{\ominus}$$

$$NH + CH_3SH \longrightarrow >\overset{\oplus}{N}H_2 \quad \text{(iv)}$$
$$\phantom{xxxxxxxxxxxxxxx} SCH_3^{\ominus}$$

$$R-CHO + H_2S \longrightarrow R-\underset{OH}{\overset{SH}{\underset{|}{C}H}} \quad \text{(v)}$$

$$R-CHO + NH_3(\text{or } NH_4OH) \longrightarrow R-\underset{ONH_4}{\overset{OH}{\underset{|}{C}H(vi)}}$$

or $R-CHO + NH_3 \longrightarrow R-CH=NH + H_2O$ in which R represents —CHO.

When the specific deodorizer is incorporated into the gel, therefore, the deodorization reactions similar to the above equations (i) to (vi) take place and proceed to on the surface of the resultant gel.

The commercially available Epoleon N-100 type deodorizer used in the following examples has the specific composition as mentioned below:

| | |
|---|---|
| ethanaminium N-(carboxymethyl)-2-hydroxy-N,N-bis(2-hydroxyethyl) chloride | 15% by weight |
| diethanolamine | 5% by weight |
| triethanolamine | 2.5% by weight |
| glyoxal | 2% by weight |
| sodium citrate | 5% by weight |
| sodium dihydrogen phosphate | 6% by weight |
| water | 64.5% by weight |

This invention is further illustrated with reference to the following Examples to which this invention is in no way limited and which demonstrate an excellent deodorization efficiency of the gel-like deodorant composition of this invention.

EXAMPLE 1

Formation of gel

Four sodium polyacrylates of different molecular weight were used as gel forming substances and polyethylene glycol diglycidyl ether used as glycidyl ether (gelling agent i.e. crosslinking agent), and the gelled state of the resultant gel was shown in Table 2 below. Sample Nos. a and b in Table 2 were referred to as comparative Example. The condition of gelation was conducted at 55° C. for 24 hours. Table 2 is clearly illustrative of the relationship between the molecular weight of sodium polyacrylate and the gelled state thereof.

EXAMPLE 2

Three types of sodium polyacrylates having a molecular weight of 40,000, 140,000 and 280,000 were used as gel forming substance, polyethylene glycol diglycidyl ether used as gelling agent, and into the resultant gel was incorporated the commercially available Epoleon N-100 type deodorizer which showed a higher deodorization activity amongst seven deodorizers as disclosed in Table 1 above. The gelled state of the resultant gel was then shown in Table 3 below. This Table was also illustrative of the relationship between the gelling agent and deodorizer, which acted on the gelled state of the resultant gel. As obviously viewed from Table 3, if the

TABLE 2

| Sample No. | Sodium polyacrylate Molecular weight | Sodium polyacrylate Proportion (% by weight) | Glycidyl ether Proportion (% by weight) | Water Proportion (% by weight) | Gelled state |
|---|---|---|---|---|---|
| Comparative | | | | | |
| a | 10,000 | 20 | 2 | 78 | Not gelled |
| b | " | 40 | 10 | 50 | Good |
| Example | | | | | |
| c | 40,000 | 6 | 2 | 92 | Non-flowable state |
| d | " | 6 | 5 | 89 | Non-flowable state |
| e | " | 7 | 2 | 91 | Good |
| f | " | 8 | 2 | 90 | Good |
| g | 140,000 | 5 | 2 | 93 | Non-flowable state |
| h | " | 5 | 5 | 90 | Non-flowable state |
| i | " | 6 | 2 | 92 | Good |
| j | " | 7 | 2 | 91 | Good |
| k | 280,000 | 3 | 2 | 95 | Good |
| l | " | 4 | 2 | 94 | Good |

As mentioned above, the gel-formed deodorant composition has a remarkable advantage that we can make a precise decision visually as to when it should be replaced with a new one. Thus, it is preferred that the deodorant composition in the form of gel is totally exhausted to be free of the residue at the final use stage, but it is impossible to do this.

When the specific gelling agent is to be used in the preparation of gel, it is preferable to select the gel forming substance which is capable of gelling by using as least a proportion of the gelling agent as possible. Accordingly, it is the use of sodium polyacrylates having a molecular weight of 40,000, 140,000 and 280,000 that we should select from the result of Table 2 above.

deodorizer in question was used in an increased amount, sodium polyacrylates and polyethylene glycol diglycidyl ether had to proportionally be used in increased amounts in order to obtain a completely gelled product. Hence, the desired gel typed deodorant composition could be obtained by selecting the proportion of the deodorizer dependent upon the intensity of malodor gas to be deodorized and also by selecting suitably the conditions of gelation.

TABLE 3

| Sample No. | Sodium polyacrylate Molecular weight | Sodium polyacrylate Proportion (% by weight) | Glycidyl ether Proportion (% by weight) | Deodorizer Proportion (% by weight) | Water Proportion (% by weight) | Gelled state |
|---|---|---|---|---|---|---|
| 1 | 40,000 | 7 | 2 | 5 | 86 | Good |
| 2 | " | 21 | 6 | 20 | 53 | Good |
| 3 | " | 28 | 8 | 30 | 34 | Good |
| 4 | 140,000 | 6 | 2 | 10 | 82 | Good |
| 5 | " | 6 | 2 | 20 | 72 | Good |
| 6 | " | 12 | 4 | 30 | 54 | Good |
| 7 | " | 24 | 8 | 40 | 28 | Good |
| 8 | 280,000 | 3 | 2 | 10 | 85 | Good |
| 9 | " | 6 | 4 | 20 | 70 | Good |
| 10 | " | 12 | 8 | 40 | 40 | Good |

In table 3 above, polyethylene glycol diglycidyl ether was used as glycidyl ether. Now, polyethylene glycol diglycidyl ether was respectively replaced with ethylene glycol diglycidyl ether, polypropylene glycol diglycidyl ether, polyglycerol polyglycidyl ether and glycerol polyglycidyl ether to observe the gelled state of the resulting gel, and it was found to be good.

Further, sodium polyacrylate was substituted with ammonium polyacrylate to check the behavior of the resultant gel and thereby gel typed deodorant composition of similar properties could be obtained.

EXAMPLE 3

The gel employed for the deodorization test was prepared as follows: The gel sample was formed under the condition of Sample No. 5 as given in Example 2, and cut into a size having a weight of 2.0 g. The test procedure employed was as follows: Four types of gases such as ammonia (alkaline smell), trimethylamine (alkaline smell), hydrogen sulfide (acidic smell) and methylmercaptan (acidic smell) were respectively used as offensive smelling gases to be tested for deodorization, and each of these malodor gases and 2.0 g of the gel-formed deodorant composition according to this invention (Sample No. 5) were charged into a 500 ml conical flask to examine the relationship between the time elapse (hour) and deodorization rate (%). The deodorization test was conducted respectively at temperatures of 4° C. which was maintained by allowing the content-filled flask to stand in a refrigerator, 25° C. which was kept by allowing the flask to stand in a room, and 50° C. which was retained by allowing the flask to stand in a thermostatic chamber. The commercially available deodorizer product was also used for single-point test as the comparative one. As the blank test, the gel sample was formed under the condition of Sample No. i as occurring in Table 2, and cut into a size having a weight of 2.0 g, as done in the gel of Sample No. 5.

The test results concerning deodorization rate (%) against different malodor gases were as follows:

| Time elapsed | 1 hr | 2 hr | 3 hr | 6 hr |
|---|---|---|---|---|
| (1) Deodorization rate (%) for ammonia gas ||||
| Tested at 4° C. and at an initial gas concentration of 3300 ppm. ||||
| Sample No. 5 | 55 | 68 | 73 | 80 |
| Commercial product | 45 | 52 | 53 | 50 |
| Sample No. i | 45 | 50 | 55 | 55 |
| Tested at 25° C. and at an initial gas concentration of 7000 ppm. ||||
| Sample No. 5 | 72 | 79 | 80 | 84 |
| Commercial product | 48 | 45 | 39 | 39 |
| Sample No. i | 50 | 52 | 47 | 48 |
| Tested at 50° C. and at an initial gas concentration of 16000 ppm. ||||
| Sample No. 5 | 79 | 87 | 87 | 90 |
| Commercial product | 13 | 33 | 30 | 38 |
| Sample No. i | 20 | 35 | 40 | 40 |
| (2) Deodorization rate (%) for trimethylamine gas ||||
| Test at 4° C. and at an initial gas concentration of 20 ppm. ||||
| Sample No. 5 | 75 | 78 | 80 | 85 |
| Commercial product | 37 | 41 | 41 | 40 |
| Sample No. i | 36 | 44 | 43 | 43 |
| Tested at 25° C. and at an initial gas concentration of 30 ppm. ||||
| Sample No. 5 | 80 | 83 | 87 | 90 |
| Commercial product | 30 | 33 | 32 | 32 |
| Sample No. i | 31 | 34 | 32 | 35 |
| Tested at 50° C. and at an initial gas concentration of 60 ppm. ||||
| Sample No. 5 | 85 | 87 | 87 | 92 |
| Commercial product | 27 | 30 | 25 | 20 |
| Sample No. i | 30 | 35 | 30 | 30 |
| (3) Deodorization rate (%) for hydrogen sulfide gas ||||
| Tested at 4° C. and at an initial gas concentration of 900 ppm. ||||
| Sample No. 5 | 92 | 98 | 99 | 100 |
| Commercial product | 28 | 33 | 35 | 67 |
| Sample No. i | 0 | 0 | 3 | 5 |
| Tested at 25° C. and at an initial gas concentration of 700 ppm. ||||
| Sample No. 5 | 95 | 97 | 99 | 100 |
| Commercial product | 30 | 48 | 63 | 90 |
| Sample No. i | 0 | 1 | 7 | 10 |
| Tested at 50° C. and at an initial gas concentration of 600 ppm. ||||
| Sample No. 5 | 91 | 96 | 97 | 99 |
| Commercial product | 23 | 55 | 62 | 92 |
| Sample No. i | 1 | 4 | 10 | 12 |
| (4) Deodorization rate (%) for methylmercaptan gas ||||
| Tested at 4° C. and at an initial gas concentration of 15 ppm. ||||
| Sample No. 5 | 50 | 80 | 90 | 100 |
| Commercial product | 0 | 0 | 0 | 0 |
| Sample No. i | 0 | 0 | 0 | 0 |
| Tested at 25° C. and at an initial gas concentration of 20 ppm. ||||
| Sample No. 5 | 50 | 65 | 80 | 95 |
| Commercial product | 0 | 0 | 0 | 0 |
| Sample No. i | 0 | 0 | 0 | 0 |
| Tested at 50° C. and at an initial gas concentration of 30 ppm. ||||
| Sample No. 5 | 30 | 40 | 55 | 80 |
| Commercial product | 5 | 10 | 25 | 30 |
| Sample No. i | 0 | 0 | 0 | 0 |

From the results of a series of deodorization tests as mentioned above, it is clear that the gel-formed deodorant composition of Sample No. 5 according to this invention is very effective for deodorization against not only acidic odor-generating substances such as hydrogen sulfide and methylmercaptan but also alkaline odor-generating substances such as ammonia and trimethylamine, and that the nitrogen-containing malodor gas, namely $NH_3$ or TMA is likely to be absorbed in the gel of Sample No. i (blank product), whereas the sulfur-containing malodor gas, namely $H_2S$ or MeSH is almost never absorbed in the gel of Sample No. i.

EXAMPLE 4

The gel typed deodorant composition of Sample No. 5 according to this invention used in Example 3 was employed for monitor test monitoring the deodorization activity in household refrigerators. The monitor test was carried out on the following conditions.

(1) Deodorizer: 100 g of gel-formed deodorant composition of Sample No. 5 were charged into a plastic container (60 mm in diameter) which was then tightly closed and uncovered in use.

(2) Objects for deodorization test: Refrigerators for domestic use (200 l in volume)

(3) Test period: Continuous use for a period of one month (4) Determination method: The deodorization activity was determined by feelings of the panellers who were mainly using said refrigerators (housewives in most cases), namely by panel test. Some deodorizer for refrigerator chambers had been used in most homes, which had been eliminated at the start of monitor test. Accordingly, the determination of the deodorization effect corresponded to the comparison between the gel typed deodorant composition according to this invention and the commercial product previously employed.

(5) Determination criteria: The grading of determination was as follows.

| | |
|---|---|
| a | There was no malodor or there was little malodor. (deodorization efficiency is remarkably noticed) |
| b | Malodor was alleviated. (deodorization efficiency is noticed) |
| c | Unchanged. (no deodorization effect is found) |
| d | Malodor was increased. (a reverse effect is produced or the deodorant composition tested has a lower deodorization effect than that used heretofore) |

(6) Number of monitor test: 30 homes
The results of monitor test were summarized in Table 4 below.

TABLE 4

| Grading | Determined number after 1 day | Determined number after 1 month |
|---|---|---|
| a | 18 | 10 |
| b | 9 | 15 |
| c | 3 | 5 |
| d | 0 | 0 |

As obvious from Table 4 above, the deodorization activity of the deodorant composition according to this invention is found in 80% or more of the total homes even after one month.

As mentioned above, the gel-formed deodorant composition according to this invention is particularly effective as a fixed deodorizer for deodorization of enclosed living spaces such as buildings and transport facilities and of tightly closed instruments, because the chemical reaction typed deodorizer is incorporated into the gel, the former has an excellent deodorization activity against different malodors.

What we claim is:

1. A deodorant composition in the form of a gel, which comprises 2% to 30% by weight of sodium polyacrylate or ammonium polyacrylate having a molecular weight of from 40,000 to 300,000, 1% to 10% by weight of diglycidyl ether or polyglycidyl ether, 5% to 40% by weight of deodorizer containing as active ingredients ethanaminium N-(carboxymethyl)-2-hydroxy-N,N,bis(2-hydroxyethyl) chloride, diethanolamine, triethanolamine, glyoxal, sodium citrate and sodium dihydrogen phosphate, and the remainder of water.

2. A deodorant composition according to claim 1 wherein aid diglycidylether is selected from the group consisting of ethylene glycol diglycidyl ether, polyethylene glycol diglycidyl ether, propylene glycol diglycidyl ether, polypropylene glycol diglycidyl ether and neopentyl glycol diglycidyl ether and said polyglycidyl ether is selected from the group consisting of trimethylolpropane polyglycidyl ether, polyglycerol polyglycidyl ether, glycerol polyglycidyl ether and diglycerol polyglycidyl ether.

3. A deodorant composition according to claim 1 wherein the deodorizer being used comprises as active ingredients 5 to 20% by weight of ethanaminium N-(carboxymethyl)-2-hydroxy-N,N-bis(2-hydroxyethyl)-chloride, 1 to 10% by weight of diethanolamine, 0.5 to 5% by weight of triethanolamine and 0.5 to 5% by weight of glyoxal, 0.5 to 5% by weight of sodium citrate and 1 to 10% by weight of sodium dihydrogen phosphate.

* * * * *